United States Patent

Nutter et al.

[11] Patent Number: 5,827,895
[45] Date of Patent: Oct. 27, 1998

[54] HEXAHYDROLUPULONES USEFUL AS ANTICANCER AGENTS

[75] Inventors: Louise Nutter; Emily O. Ngo; Thomas Stephan, all of Minneapolis; Gilbert J. Mannering, St. Paul, all of Minn.

[73] Assignee: Regents of the University of Minnesota, Minneapolis, Mich.

[21] Appl. No.: 717,120

[22] Filed: Sep. 20, 1996

Related U.S. Application Data

[63] Continuation-in-part of Ser. No. 607,473, Feb. 27, 1996, abandoned.

[51] Int. Cl.$^6$ .................................................. A61K 31/12
[52] U.S. Cl. .................................... 514/690; 424/405
[58] Field of Search .................... 424/405, 451; 514/690; 435/883, 864

[56] References Cited

U.S. PATENT DOCUMENTS

| | | | |
|---|---|---|---|
| 4,140,122 | 2/1979 | Kuhl et al. ........................... | 128/260 |
| 4,383,529 | 5/1983 | Webster ............................... | 604/20 |
| 4,450,270 | 5/1984 | Lunn .................................... | 544/24 |
| 4,590,296 | 5/1986 | Cowles et al. ........................ | 568/366 |
| 4,668,504 | 5/1987 | Kahan et al. .......................... | 424/10 |
| 4,783,453 | 11/1988 | Christensen ........................ | 514/210 |
| 4,918,240 | 4/1990 | Todd, Jr. et al. ..................... | 568/366 |
| 4,921,857 | 5/1990 | Heck .................................... | 514/254 |
| 4,931,279 | 6/1990 | Bawa et al. ........................... | 424/427 |
| 5,082,975 | 1/1992 | Todd, Jr. et al. ..................... | 568/315 |
| 5,262,151 | 11/1993 | Montgomery ......................... | 424/50 |
| 5,286,506 | 2/1994 | Millis et al. .......................... | 426/335 |
| 5,370,863 | 12/1994 | Barney ................................. | 424/49 |
| 5,455,038 | 10/1995 | Barney ................................. | 424/405 |

OTHER PUBLICATIONS

J. F. Carson, "The Hydrogenatio ofLupulone and Humulone", *J. Amer. Chem. Soc.*, 73, 1850–1852, (1951).

Gilbert J. Mannering, et al., "Effects of the Hop Component, Colupulone, on the Induction of Cytochrome P4503A and the Replication of Human Tumour Cells", *Food, Nutrition and Chemical Toxicity*, Parke et al., eds., Smith Gordon G.B., Chapter 28, 311–323, (1993).

Ken Yasukawa, et al., "Humulon, a Bitter in the Hop, Inhibits Tumor Promotion by 12–0–Tetradecanoylphorbol–13–Acetate in Two–Stage Carcinogenesis in Mouse Skin", *Oncology*, 52, 156–158, (1995).

Mizobuchi, S., et al., "Antifungal Activities of Hop Bitter Resins and Related Compounds", *Res. Lab. Kirin Brew. Co.*, No. 28, pp. 39–44, (1985).

*Primary Examiner*—Gollamudi S. Kishore
*Attorney, Agent, or Firm*—Schwegman, Lundberg, Woessner & Kluth, P.A.

[57] ABSTRACT

The present invention provides pharmaceutical compositions comprising an amount of hydrogenated lupulones or derivatives or analogs thereof, effective to inhibit cancer cell and/or bacterial cell growth, and methods of use thereof.

18 Claims, 2 Drawing Sheets

HEXAHYDROLUPULONES USEFUL AS ANTICANCER AGENTS

This application is a continuation-in-part of U.S. Ser. No. 08/607,473 (filed Feb. 27, 1996) now abandoned.

BACKGROUND OF THE INVENTION

The treatment and/or cure of cancer has been intensely investigated culminating in a wide range of therapies. Cancer has been typically treated with surgery, radiation and chemotherapy, alone or in conjunction with various therapies employing drugs, biologic agents, antibodies, and radioactive immunoconjugates, among others. The common goal of cancer treatment has been, and continues to be, the elimination or amelioration of cancerous tumors and cells with minimal unpleasant or life-threatening side effects, due to toxicity to normal tissues and cells. However, despite efforts, these goals remain largely unmet.

Even where effective non-invasive drug therapies have been developed, patients having solid malignant tumors and hematological malignant disorders often develop multidrug resistance. Current therapies involve the administration of increased dosages of the anticancer drug or drugs to which the cancer cells have become resistant and/or administration of agents designed to reverse drug accumulation defects in drug resistant cells. However, these therapies are limited by risk of toxicity to the patient.

Alpha- and beta-acids, derived from hops, possess the ability to inhibit the growth of microorganisms. Some of these acids have been used as antibiotic and antifungal agents. In addition, alpha acids (also known as humulons) have been shown to inhibit the tumor promoting effect of 12-O-tetradecanoylphorbol-13-acetate in mice (Yasukawa et al., *Oncology* 52:156–158 (1995)). Colupulone has been reported to be active against Hela cells, CEM leukemia cells, and adriamycin- and vinblastin-resistant CEM cells (Mannering et al., *Food, Nutrition and Chemical Toxicity*, Parke et al., eds, Smith Gordon, G. B. (1993) at ch. 28).

However, a continuing need exists for new and effective drug therapies for treating cancer which have minimal side effects and are also effective against multidrug resistant cancer cells.

In addition, the cases of bacteria resistant to one or more antibiotic drugs has increased dramatically. *Staphylococcus Aureus* and enterococcus are among the most problematic of these drug resistant bacteria in the clinic. For example, methicillin resistant *Staphylococcus Aureus* (MRSA) was previously treatable by ciprofloxacin (CIPRO). However, cases of CIPRO resistant MRSA are rapidly increasing. In addition, reports of vancomycin resistant enterococcus (VRE) in the U.S. have increased. Vancomycin is used as an antibiotic for treatment of bacteria resistant to penicillins and aminoglycosides, and is considered by many as the last rational resort for therapy of these resistant bacteria. Alternatives to vancomycin, such as chloramphenicol, have less favorable therapeutic indices and are usually ineffective.

Tuberculosis (TB), caused by mycobacterium tuberculosis, results in more deaths worldwide than any other disease caused by infectious agents. It is estimated that 1.7 billion persons, or 33% of the world population, are currently infected with TB, 8 million of which develop active TB. Within the U.S. alone, 15 million persons have latent TB, with the number of cases increasing by 14% since 1993. The reasons for this increase in TB primarily relate to AIDS, immunocompromised states (e.g., cancer chemotherapy and transplant recipients) and drug resistance to available anti-TB drugs.

Thus, a need exists for new and effective drug therapies for treating bacterial infections, particularly therapies effective against multidrug resistant bacteria.

SUMMARY OF THE INVENTION

The present invention provides a method to inhibit cancer cell growth, and thereby to treat cancer comprising administering to a mammal afflicted with cancer an effective amount of the compound wherein R is —$CH_2CH(CH_3)_2$, —$CH(CH_3)_2$, or —$CH(CH_3)CH_2CH_3$, or a pharmaceutically acceptable salt thereof. In a preferred embodiment of the invention, R is —CH(CH3)2. The present invention further provides a method of inhibiting bacterial cell growth by contacting bacterial cells with an effective amount of a compound of formula (I). The present invention also provides pharmaceutical compositions comprising an effective amount of a compound of formula (I) in combination with a pharmaceutically acceptable carrier.

DETAILED DESCRIPTION OF THE INVENTION

The present invention provides a method of killing cancer cells and/or inhibiting their growth through the use of certain β-acids. In a preferred embodiment, the method utilizes lupulones or analogs thereof. Generally preferred are hydrogenated derivatives of lupulones, e.g., compounds of the formula wherein R is —$CH_2CH(CH_3)_2$ (hexahydrolupulone), —$CH(CH_3)_2$ (hexahydrocolupulone or "HHC"), or —$CH(CH_3)CH_2CH_3$ (hexahydroadlupulone), or a pharmaceutically acceptable salt thereof. In a preferred embodiment of the invention, R is —$CH(CH_3)_2$. The compounds may also be administered as a mixture comprising one or more compounds of formula (I). The tautomeric forms of the compounds of formula (I) are also within the scope of the present method.

Beta-acids (also known as lupulones), and tetrahydroisohumulone and hexahydrocolupulone in particular, can inhibit the growth of food pathogens, such as *Listeria monocytogenes* (U.S. Pat. Nos. 5,286,506; 5,455,038). In addition, hexahydrolupulone inhibits the growth of certain Lactobacilli (U.S. Pat. No. 5,082,975). However, the antineoplastic effects of hydrogenated lupulones have not been previously reported.

These compounds have been found to be highly effective cytostatic and cytotoxic agents which are active against cells of a wide variety of cancers. For example, hexahydrocolupulone has been found to have cytotoxic and/or cytostatic effect against human breast adenocarcinoma cells, human acute lymphoblastic leukemia cells, vinblastin resistant cells, human Burkitt lymphoma cells, human oral epidermoid carcinoma cells, and human cervical epithelioid carcinoma cells.

Hexahydrocolupulone (HHC) has also demonstrated effectiveness against drug resistant human cancer cell lines, for example, vinblastin resistant human acute lymphoblastic leukemia cells. Multidrug resistance against anticancer compounds is one of the most formidable problems in cancer chemotherapy. In addition to their broad spectrum anticancer activity, the compounds of the present invention have potential clinical application due to their high potency, as shown by their relatively low $IC_{50}$ concentrations ($IC_{50}$ represents the concentration of compound required to kill 50% of cancer cells in an in vitro assay). Moreover, as a derivative of a generally-recognized safe hop extract, HHC can be considered negligibly toxic when ingested, an advantage over many existing chemoagents.

Hydrogenated lupulones appear to be more active and stable than their non-hydrogenated parent compounds. For example, hexahydrocolupulone is more active than colupulone (see Mannering et al., cited supra) while hexahydrolupulone has been found to be more stable than lupulone (Carson, *J. Amer. Chem. Soc.* 73:1850–1852 (1951)).

According to the invention, cancer cells are inhibited by administration to a mammal afflicted with cancer of an effective amount of the compounds of Formula (I). The "effective amount" will ultimately depend upon whether inhibition of growth or killing of cancer cells is goal of the treatment. However, as described herein, a suitable dose will be in the range of about 0.5 to about 100 mg/kg of body weight per day.

The compositions described herein are believed to be effective in the treatment of solid mammalian tumors or hematologic malignancies, and include those which can develop multidrug resistance. These solid tumors include cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; and melanoma of cutaneous and intraocular origin. Hematological malignancies include childhood leukemia and lymphomas, Hodgkin's disease, lymphomas of lymphocytic and cutaneous origin, acute and chronic leukemia, plasma cell neoplasm and cancers associated with AIDS. The preferred mammalian species for treatment are humans and domesticated animals.

Without being bound by any particular theory regarding mechanism of action, preliminary results using the fluorescent activated cell sorting (FACS) method suggest that HHC has an effect upon the G1-S phase transition of the cell cycle. Other studies suggest that the cytotoxic effect of HHC on cancer cells is not due to major effects upon DNA, RNA or protein synthesis.

In another embodiment of the invention, a compound of formula (I), or a salt or pharmaceutical composition thereof, is used to inhibit bacterial cell growth. In a preferred method, the bacteria is a gram positive bacteria. In a more preferred embodiment, the gram positive bacteria is *Staphylococcus Aureus*. The compounds are also effective in inhibiting the growth of drug resistant bacteria, including those strains resistant to methicillin, ciproflaxacin, vancomycin, chloramphenicol, penicillin, aminoglycosides, erythromycin, cephalothin, cloxacillin, tetracycline and/or chloramphenicol. In a preferred method, the compounds are used to inhibit the growth of drug resistant *Staphylococcus Aureus*. The compounds are also effective in inhibiting the growth of vancomycin resistant enterococcus.

In another embodiment of the invention, the compounds are used to inhibit the growth of mycobacteria. In a more preferred embodiment, the mycobacteria is tuberculosis. The compounds are also effective in inhibiting the growth of drug resistant mycobacteria, including those strains resistant to isoniazid, rifampin, pyrazinamide and/or ethambutol. In a preferred method, the compounds are used to inhibit the growth of drug resistant tuberculosis.

In another embodiment of the invention, a compound of formula (I), or a salt or pharmaceutical composition thereof, is used to inhibit the growth of protozoa, particularly parasitic protozoa. In a preferred embodiment, the protozoa is *Leischmanial*. In another embodiment of the invention, a compound of formula (I), or a salt or pharmaceutical composition thereof, is used to inhibit the growth of fungii, such as systemic and superficial mycoses.

Hexahydrolupulones are hydrogenated derivatives of lupulones, a constituent of hops (up to 5–7%). Hexahydrocolupulone can be made via the chemical hydrogenation of colupulone using a number of methods known in the art. For example, hydrogenation can be achieved with platinum (IV) oxide as a catalyst as described by Riedl (*Ber.* 89:1863 (1956)) or by Carson (*J. Am. Chem. Soc.* 73:1850 (1951)).

In a preferred method, beta-acids are purified as described in U.S. Pat. No. 4,918,240 and hydrogenated as described in U.S. Pat. No. 5,082,975 (both of which are herein incorporated in their entireties). According to a preferred method of purifying beta acids, palladium or platinum catalyst poisons are removed from an aqueous alkaline beta acid solution by agitating the solution at a pH of at least about 10, preferably between about 11 and 12.9, in the presence of polyvalent metals other than palladium and platinum. The insoluble catalyst poison containing materials are then separated.

Preferably, the polyvalent metals used are edible metal ions, preferably magnesium and calcium, and may also be zinc, aluminum or iron. Preferably, the pH is between about 11 and 12.9. Although a solvent is not necessary for removal of the catalyst poisons, water-immiscible food-grade solvents may be used. Examples include hydrocarbons such as hexane, esters, liquid fatty alcohols, and terpenes such as limonen.

In preparation for the ensuing hydrogenation step, the purified beta acids may be recovered from the alkaline aqueous phase by the $CO_2$ method of Cowles (U.S. Pat. No. 4,590,296). Alternatively, the beta-acid solution is mixed with about an equal volume of an organic solvent such as hexane. The beta-acids are extracted into solvent by slow acidification with agitation, using an acid such as phosphoric acid, until a pH of about 9.5–9.8 is reached. Substantially all of the beta acids are removed from the aqueous phase by this procedure. The beta acids may then be recovered from the solvent by partial evaporation and cooling, or by removal of the hexane under vacuum, by procedures known to the art.

Any known method of hydrogenation may be used, although preferably one is used which results in a high purity of beta acids. Preferably, the purified beta-acids are hydrogenated under non-acidic conditions. According to a preferred method, the beta-acids are dissolved in solvent and water. Any non-toxic, non-reactive solvent may be used such as lower alkanols, an organic water miscible or THF. A hydrogenation catalyst such as palladium or platinum is added. The vessel is evacuated, hydrogen gas is introduced, and the vessel is agitated until hydrogen uptake has ceased. The hydrogenated product is filtered to remove the catalyst. A solution of water and a hydrocarbon solvent such as hexane is then added. The mixture is agitated and the hydrogenated beta acid is extracted into the hexane phase. After partial evaporation of the hexane, the mixture is seeded and cooled, allowing the product to crystallize.

To allow conversion to pure hydrogenated beta acids, the minimum pH used is about 3, preferably above 4, with the most preferred range between about 7 to 9. The rate of hydrogenation may be accelerated through the use of additional amounts of catalyst or by raising the temperature.

An aqueous liquid alkaline solution of hydrolupulones may be prepared as described in U.S. Pat. No. 5,082,975. Alternatively, propylene glycol, glycerine, similar stable alcohols and polyols, or mixtures thereof with or without water, may be substituted for the water of the aqueous solution. In addition, the foregoing aqueous solution may be mixed with glycol or glycerine, etc., to form a standardized solution of product, which is readily-dispersible in water, and stable as well.

Pharmaceutically acceptable salts of the biologically active compounds described herein may be used as well in practicing the claimed methods. Pharmaceutically acceptable salts may be formed using organic or inorganic based, such as NaOH, Na(CO$_3$)$_2$, NaHCO$_3$, KOH and the like.

Although the compounds described herein and/or their its salts may be administered as the pure chemicals, it is preferable to present the active ingredient as a pharmaceutical composition. The invention thus further provides the use of a pharmaceutical composition comprising one or more compounds and/or a pharmaceutically acceptable salt thereof, together with one or more pharmaceutically acceptable carriers therefor and, optionally, other therapeutic and/or prophylactic ingredients. The carrier(s) must be 'acceptable' in the sense of being compatible with the other ingredients of the composition and not deleterious to the recipient thereof.

Pharmaceutical compositions include those suitable for oral or parenteral (including intramuscular, subcutaneous and intravenous) administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration may be presented as discrete unit dosage forms such as hard or soft gelatin capsules, cachets or tablets each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art., e.g., with enteric coatings.

Oral liquid preparations may be in the form of, for example, aqueous or oily suspension, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservative.

The compounds may also be formulated for parenteral administration (e.g., by injection, for example, bolus injection or continuous infusion) and may be presented in unit dose form in ampules, pre-filled syringes, small bolus infusion containers or in multi-does containers with an added preservative. The compositions may take such forms as suspensions, solutions, or emulsions in oily or aqueous vehicles, and may contain formulatory agents such as suspending, stabilizing and/or dispersing agents. Preferable, the liquid carrier is a non-alkaline solution. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in Fisher et al. (U.S. Pat. No. 4,788,603) or Bawas et al. (U.S. Pat. No. 4,931,279, 4,668,504 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4383,529, or 4,051,842.

Compositions suitable for topical administration in the mouth include unit dosage forms such as lozenges comprising active ingredient in a flavored base, usually sucrose and acadia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention may also contain other adjuvants such as flavorings, coloring, antimicrobial agents, or preservatives.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The following examples are intended to illustrate but not limit the invention.

EXAMPLES

Example I—Cytostatic Activity

HHC was tested for cytostatic activity using the trypan blue exclusion assay. The purpose of the assay is to determine the concentration of HHC at which 50% of cell growth is inhibited (i.e., $ID_{50}$) when cells are continuously exposed to the HHC. Five ml of a mixture of $2\times10^5$ cells/ml were placed in T-25 flasks. HHC or control (no HHC or DMSO vehicle) was added. The cells were incubated at 37° C. under 5% $CO_2$ for 24 or 48 hours. Monolayer cells which are attached need to be incubated for a minimum of 14 hours before HHC is added in order to allow the cells to attach. The cells are detached by pancreatinizing (attached cells) and or suspended well (unattached cells). A 100 $\mu$l sample was removed from the cell suspension and placed in a borosilicate glass test tube. One hundred $\mu$l of 0.4% trypan blue solution (trypan blue (Sigma) in phosphate buffered saline) was added to the cell suspension sample and mixed well. The cells were counted using a hemocytometer. $ID_{50}$ was calculated by choosing a drug concentration that was below 50% inhibition as well as a drug concentration that was above 50% inhibition and then interpolating those values to 50% inhibition. The following formula was used:

% inhibition=100-growth, where % growth=$[(C_t-C_0)/(C_{ct}-C_0)]\times100$, where $C_0$ is the cell count at time "0";

$C_t$ is the cell count of the HHC treated sample at time "t"; and $C_{ct}$ is the cell count of the control sample at time "t".

Table I presents data on the activity of HHC against various cancer cell lines. MCF-7 cells are human breast adenocarcinoma cells which have some characteristics of differentiated mammary epithelium (i.e., dome formation and estradiol processing via cytoplasmic estrogen receptors). CEM cells are human acute lymphoblastic leukemia cells which morphologically resemble lymphoblastic cells. CEM vinblastin resistant cells contain the P-glycoprotein therefore enabling them to exhibit multidrug resistance to many structurally unrelated compounds. Raji cells are human Burkitt lymphoma cells which are lymphoblast-like. KB cells are human oral epidermoid carcinoma cells. HeLa S3 cells are human cervical epithelioid carcinoma cells.

TABLE I

| Cell type | no. of experiments | $ID_{50}$ ($\mu$M) | standard deviation |
|---|---|---|---|
| MCF-7[1] | 3 | 1.23 | 0.17 |
| CEM[1] | 4 | 1.97 | 0.34 |
| CEM vin resistant[1] | 4 | 2.61 | 0.33 |
| Raji[2] | 4 | 2.19 | 0.40 |
| KB[1] | 3 | 0.85 | 0.07 |
| HeLa S3[2] | 3 | 1.21 | 0.03 |

[1]period of incubation = 48h; [2]period of incubation = 24h.

As the results indicate, HHC is an effective and potent cytostatic agent with respect to a wide variety of cancer cell types.

Example II—Cytotoxic Activity

HHC was tested for cytotoxic activity using a colony formation assay, using an 18 hour pulse exposure. The purpose of the clonogenic assay is to determine the concentration of HHC at which 50% of cell growth is inhibited (i.e., $IC_{50}$) when cells are exposed to the HHC for a defined amount of time (i.e., a pulse exposure to the xenobiotic).

Five ml of a mixture of $2\times10^5$ cells/ml (MCF-7 cells) were placed in each of 4 T-25 flasks in a media of RPMI (Gibco). The cells were incubated at 37 ° C. under 5% $CO_2$ for a minimum of 14 hours to allow the cells to attach. The cells were pulsed for 18 hours with HHC concentrations of 0, 1.5, and 25 $\mu$M, or with DMSO.

The media was removed from the flasks (i.e., media with floating cells) and placed in 15 ml polypropylene centrifuge tubes 1–4 (summarized in Table II). The flasks were washed in 1 ml of PBS and the wash was placed in the appropriate tubes 1–4. Tubes 1–4 were centrifuged at 150 rpm and the media was aspirated. Cells were detached from the flasks by pancreatinization. Approximately 1 ml of the cell suspension from the flasks were added to the appropriate tubes (1–4) and the pellet suspended. The cells in tubes 1–4 were pooled with the cells in the flask. The cells were then resuspended.

One ml of cell suspension from the flask was added to the appropriate 10x tube (tubes 5–8) along with 9 ml of media and suspended well. One ml of the suspension in each 10x tube was then placed in the appropriate 50x tube (tubes 9–12) along with 4 ml of media.

TABLE II

| | control[b] | DMSO | 1.5 $\mu$M HHC | 25 $\mu$M HHC |
|---|---|---|---|---|
| floating cells | 1a | 2 | 3 | 4 |
| 10x dilution | 5 | 6 | 7 | 8 |
| 50x dilution | 9 | 10 | 11 | 12 |

[a]tube no.
[b][HHC] = 0

The cells in the original cell suspension (i.e., in the flask) were counted using trypan blue exclusion assay (described in Example II). Based on this count, the number of cells in the 50x tubes were calculated. The volume necessary to acquire approximately 5400 cells was then determined. This volume was removed from the 50x suspension and placed into 50 ml polypropylene tubes (tubes 13–16). Media was added to attain a volume of 18 ml. The cells were then suspended.

Five ml of suspension from each of tubes 13–16 was transferred to 60×15 mm tissue culture dishes (in triplicate). The cells were incubated until colonies of at least 50 cells were present (approx. 6–8 days). The cells were then stained with Giemsa stain (a solution of 1% Giemsa stain (Sigma) in 100% methanol). The culture dishes were removed from the incubator and the media aspirated off. The dishes were washed 2x with phosphate buffered saline (3–4ml). Three to four ml of 100% ethanol was added to each dish, an amount sufficient to cover the bottom of the dish, covered and allowed to stand for 30 minutes. The stain was washed out with cold $H_2O$. The water was poured off, without loss of colonies. The plates were inverted and allowed to dry. The cells were counted in those colonies which consisted of at least 50 cells. The $ID_{50}$ was determined as described in Example II. The data is shown in Table III.

TABLE III

| Cell type | no. of experiments | $ID_{50}$ ($\mu M$) | Std. deviation |
|---|---|---|---|
| MCF-7 | 2 | 1.62 | 0.28 |

As the data shows, HHC is able to effectively kill MCF-7 cancer cells at low dosages.

Example III—In Vitro Studies

C1300 cells (mouse neuroblastoma), a murine tumor cell model which is sensitive to HHC were evaluated. Preliminary data suggests that the in vitro $ID_{50}$ of HHC in C 1300 cells is approximately 1.94 $\mu M$ after 48 hours of continuous exposure.

Example IV—Determination of Mechanism of Action

Fluorescence activated cell sorting (FACS) was used to determine what percentage of cells could be found in the designated cell cycle phase after 48 hours of continuous HHC exposure. There are four distinct phases in the cell cycle which lead to duplication of the cell and its genetic material. In the G0/G1 phase the cell is at rest or is performing miscellaneous biosynthetic functions. During the S phase, DNA synthesis occurs which leads to replication of the chromosomes. G2 is the pre-mitotic interval while the M phase is the time during which the cell divides.

MCF-7 cells were exposed to concentrations of 1.5 $\mu M$ and 25 $\mu M$ of HHC, and DMSO. DMSO had no significant effect on the cell cycle, with a profile almost identical to that of the "no drug" control. The results indicate that low [HHC]'s (i.e., 1.5 $\mu M$) increase the number of cells in G0/G1 and decrease the number of cells in S phase. At high [HHC]'s (i.e., 25 $\mu M$) there is a decrease in the number of cells in G0/G1 and an increase in the number of cells in S phase. This indicates that HHC has an apparent effect upon the G1-S phase transition of the cell cycle.

Example V—Antibacterial activity (*Staphylococcus aureus*)

Figure 1:
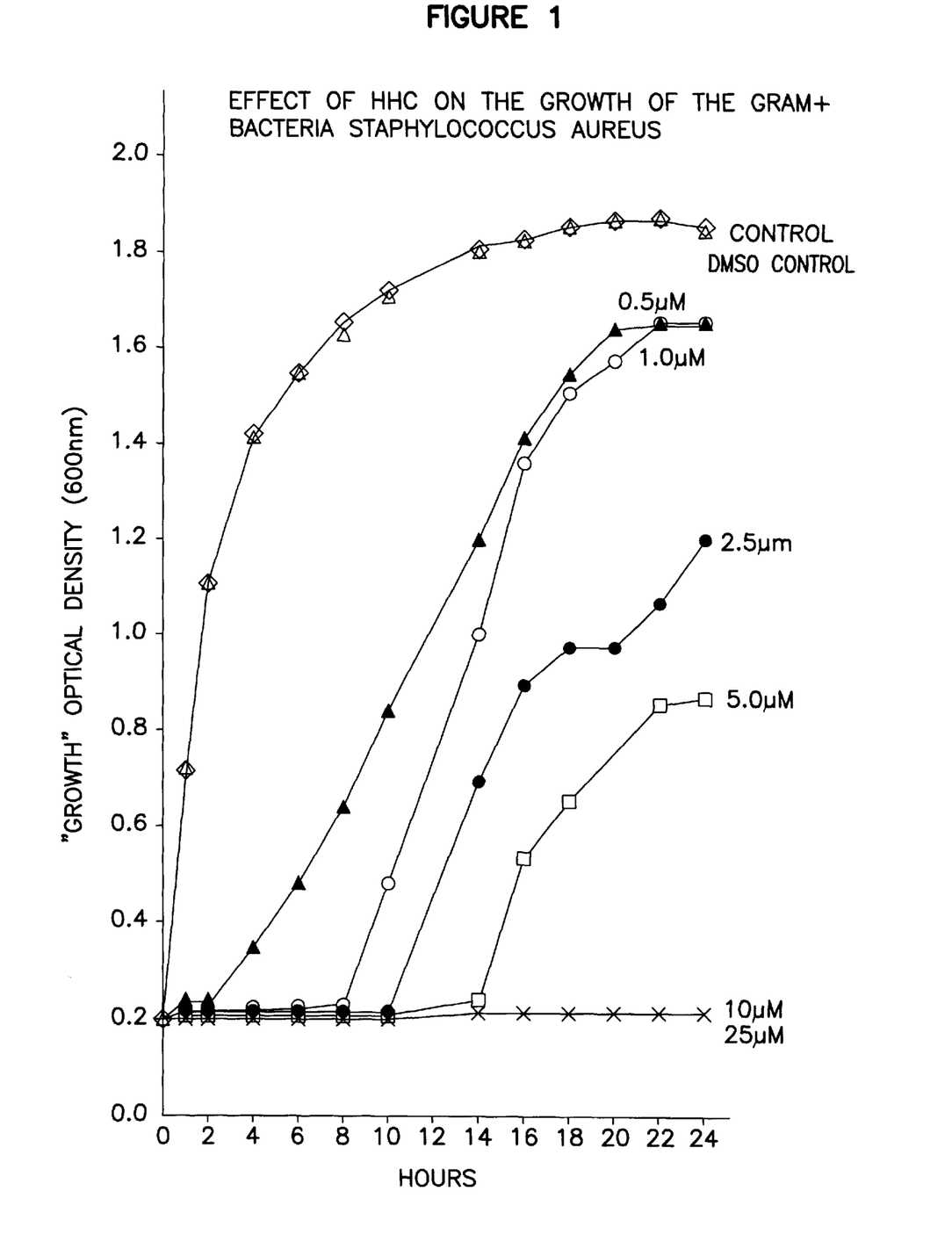
FIG. 1 shows the activity of HHC against *Staphylococcus aureus*.
Figure 2:
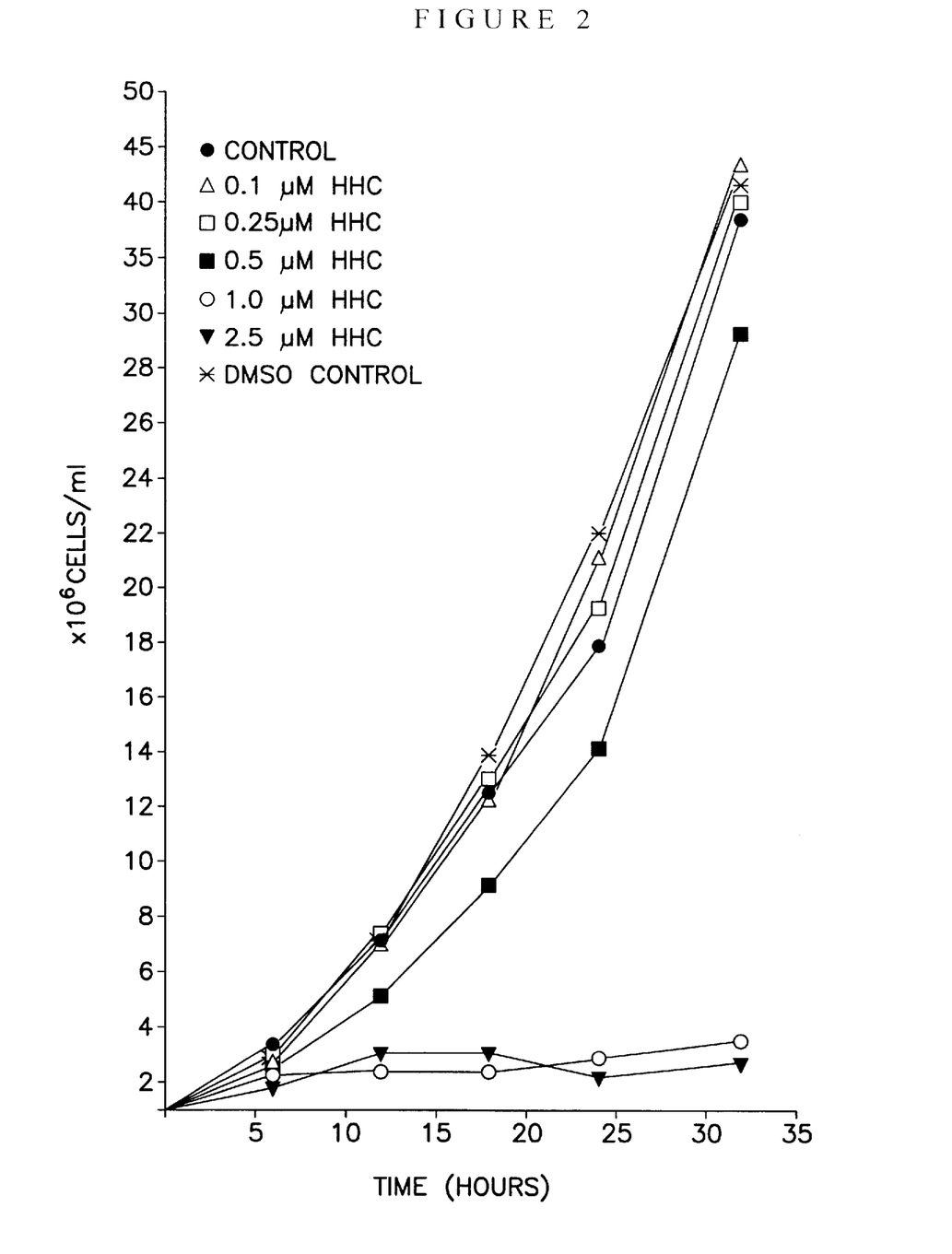
FIG. 2 shows the activity of HHC against *Leishmania tarentolae*.

A single colony of *Staphylococcus aureus* was grown in 2 ml of Luria-Bertani (LB) broth overnight at 37° C. in a bacterial shaker with vigorous shaking. 0.5 ml of the culture was transferred to 250 ml LB and allowed to grow at 37° C. until the OD600 (optical density) reading was about 0.2 (a reading of 1 OD600 indicates a cell concentration of approximately $8 \times 10^8$ cells/ml). Cultures were aliquoted into 50 ml tubes containing 13 ml of bacterial culture per tube. 0.5, 1.0, 2.5, 5.0, 10 and 25 $\mu M$ of HHC was added to the tubes. No-drug and DMSO solvent were used as controls. Aliquots of the bacterial culture were taken every 2 hours to obtain the OD600 reading. As the results indicate (FIG. 1) HHC is an effective inhibitor of bacterial growth.

The effect of HHC against various strains of laboratory quality control drug resistant bacteria was also determined. An assay was performed to determine the minimum inhibitory concentration (MIC) of HHC against methicillin resistant *Staphylococcus aureus*, coagulase-negative *Staphylococcus* and vancomycin resistant group D Enterococcus. HHC was dissolved in DMSO to achieve a working concentration of 500 $\mu M$ and then further diluted in Mueller Hinton broth (MH). The final test concentration by macrotube dilution were: 100, 50, 25, 10, 5, 2.5, 1.0, 0.5, 0.25, and 0.12 $\mu M$. The test organisms were diluted in MH broth to achieve a final concentration of $1-5 \times 10^5$ CFU/ml. MIC's were recorded as the lowest concentration of HHC completely inhibiting the organisms. The results are shown in Table IV.

TABLE IV

| EFFECT OF HHC UPON BACTERIAL GROWTH | |
|---|---|
| STRAIN | MIC (micromolar; $\mu M$) |
| Gram (+) Bacteria | |
| *Staphylococcus Aureas* | 5 $\mu M$ |
| MRSA (Methicillin resistant *Staphylococcus A.*) | 2.5 $\mu M$ |
| Multidrug resistant Staphylococcus (except to Vancomycin) | 2.5 $\mu M$ |
| VRE (Vancomycin resistant enterococcus) | 5 $\mu M$ |
| Gram (−) Bacteria | |
| *E. Coli* | >100 $\mu M$ |
| Pseudomonas | >100 $\mu M$ |

The results shown in the above table indicate the following: first, the MIC for HHC against gram (+) bacteria are within the ranges of clinically achievable levels. Second, HHC possesses a unique mechanism of action. It has been shown that drug resistant MRSA are cross resistant with other antibiotics (including erythromycin, cephalothin, cloxacillin, tetracycline and chloramphenicol); however, HHC is not. In addition, the results from studies of VRE show that HHC is not cross resistant with vancomycin. Third, the antimicrobial activity of HHC is highly specific as suggested by the activity of HHC against gram (+) but not gram(−).

HHC was also tested for effectiveness against various bacterial isolates obtained from human subjects. The results are shown in Table V.

TABLE V

Patient Isolates Evaluated for Antibiotic Sensitivity

| Patient<br>Organism | A<br>VRE | B<br>VRE | C<br>VRE | D<br>MRSA | E<br>MRSA | F<br>MRSA | G<br>OxaRSA |
|---|---|---|---|---|---|---|---|
| Amp (R > 8 µg/ml) | R | R | R | — | — | R | — |
| Ceph (R > 32 µg/ml) | — | — | — | R | R | — | R |
| Chlor | S | S | S | — | — | — | — |
| Cipro (R > 2 µg/ml) | R | R | R | R | R | R | R |
| Clin (R > 8 µg/ml) | — | — | — | R | R | — | R |
| Eryth (R > 8 µg/ml) | — | — | — | R | R | — | R |
| Gen | — | S | — | — | — | — | — |
| Oxa (R > 8 g/ml) | — | — | — | R | R | — | R |
| Pen (R > 8 g/ml) | R | R | R | R | R | R | R |
| Rif | — | S | — | — | — | S | — |
| Strep (R > 2000 µg/ml) | — | R | — | — | — | — | — |
| Tetra | S | S | — | — | — | — | — |
| Tri/Sulfa | S | — | — | — | — | — | — |
| Vanco (R > 16 µg/ml) | R | R | S | S | S | — | S |
| [HHC] µg/ml (MIC) | S | S | S | S | S | S | S |
| | 1.015 | 4.06 | 2.03 | 1.015 | 1.015 | 1.015 | 1.015 |

VRE = Vancomycin Resistant *Enterococcus faeclum*; MRSA = Methicillin Resistant *Staphylococcus aureus*; OxaRSA = Oxacillin Resistant *Staphylococcus aureus*; R = Resistant; S = Sensitive; — = not available; Amp = Ampicillin; Ceph = Cephalothin; Chlor = Chloramphenicol; Cipro = Ciprofloxacin; Clin = Clindamycin; Eryth = Erythromycin; Gen = Gentamicin; Oxa = Oxacillin; Pen = Peniciliin; Rif = Rifampin; Strep = Streptomycin; Tetra = Tetracycline; Tri/Sulfa = Trimethoprim/Sulfonamide; Vanco = Vancomycin; HHC positive control (*Staphylococcus aureus*) = 2.03 µg/ml; HHC negative control (*Escherichia coli*) = 100 µg/ml; 1.015 µg/ml HHC = 2.5 µM; 2.03 µg/ml HHC = 5 µM; 4.06 µg/ml HHC = 10 µM.

As shown, the bacterial isolates were sensitive to HHC, indicating the drug's effectiveness against bacteria resistant to a variety of antibiotics.

Example VI—Antibacterial activity (M. tuberculosis)

Drug susceptibility was tested using the BACTEC method (Siddigi, BACTEC TB System Product and Procedure Manual, Becton Dickinson Corp (1989); Inderlied, *Antimycobacterial Agents* in *Antibiotics* in *Laboratory Medicine*, ed. Lorian, 3rd edition, Williams and Wilkins). The growth curve of mycobacteria in liquid media with and without HHC was plotted for 4 to 12 days. Resistance was determined by modification of the 1% proportional method. The control vial was inoculated with a 1:100 dilution of organisms, and a growth rate greater than vials with HHC was interpreted as evidence of susceptibility. Resistance occurs where less than 99% of the organisms are inhibited by the HHC.

Materials:
1) BACTEC 12B vials
2) HHC
3) Special Diluting Fluid (DF): 0.2% fatty acid free bovine serum albumin and 0.02% polysorbate 80 in distilled water, adjusted to pH 6.8±0.2 dispensed and sterilized in the following aliquots: a) 3.0 ml with 8–10 glass beads (1–2 mm/ea); b) 1.5 ml; c) 9.9 ml; and d) 9.0 ml
4) 0.5 McFarland standard in the same tube as (3) above
5) disposable sterile culture loops
6) 1.0 ml tuberculin syringes with fixed 22–26 gauge needle
7) individually packaged alcohol wipes
8) Vortex mixer
9) ATCC 27294 (S.I.R.E. susceptible M. tuberculosis)

A quantity of growth of ATCC 27294 was removed from the solid media with a sterile applicator stick and placed in a tube with glass beads and DF. Vortex was used to emulsify bacterial clumps. 0.1 ml of this suspension was used to inoculate new, pre-gassed BACTEC vials. The vials were incubated at 37° C. and monitored daily. The culture was ready for inoculation into the HHC and control vials on the day when the growth index (GI) reached 900–999.

Vials that have been at 999 for more than one day should not be used, as the bacterial load may be too high. Control vials, inoculated with growth below an index of 900, do not reliably reach the test cutoff value of 30 in the required 12 day experimental period. Serial BACTEC-to-BACTEC transfers of the ATCC organisms are acceptable within the confines of the experimental period.

BACTEC vials were run on the BACTEC instrument to establish proper $CO_2$ levels. The HHC was inoculated aseptically (0.1 ml HHC solution/vial) into labeled vials. Each HHC vial, and one DF vial containing 9.9 ml DF, was inoculated with 0.1 ml of the ATCC BACTEC culture. The DF vial, now containing a 1:100 dilution of the bacterial suspension, was inverted 10X to mix and 0.1 ml withdrawn to inoculate the control 12B vial. A 1:10 control was made in the same manner as above, using a vial with 9.0 ml DF and 1.0 ml of the ATCC BACTEC culture. All test vials were incubated at 37° C.±1° C. for 4 to 12 days, with daily reading on the BACTEC instrument. The vials must be run at approximately the same time each day.

The test was finished when the GI of the control vial reaches 30 and at least 5 days have transpired. The change in GI from one reading to another (delta change) is indicative of the growth rate. If the change is greater in the HHC vial compared to the control, the isolate is resistant to the HHC; if about the same, the isolate is borderline in susceptibility; and if less than the control, the isolate is susceptible to HHC. If the GI in the HHC vials is initially very high (>300) and the GI in the control is low, the inoculum probably included clumps, and the test needs to be repeated. If the GI in a particular HHC vial has reached 500 and then declines when the control reaches 30, the isolate is considered resistant to HHC. If the GI in a HHC vial reaches 900 and then declines before the control reaches 30, the isolate is considered resistant. If the GI of a vial reaches 999 before the control reaches 30, the inoculum was too heavy, and the test needs to be repeated. If the GI reaches 999 on the same day as the control reaches 30, and the delta GI is greater than the control, resistance can be reported. However susceptibility cannot be determined with a reading of 999, and the test would need to be repeated. If the delta GI for the HHC vial is close (10%) to the delta GI of the control this indicates partial resistance, and additional readings (1–3 days) should be taken. The 1:10 control was not used as part of a standard 1% proportional method, but was included here to measure smaller drug effects that may not be apparent with the standard 1% method.

HHC inhibited >99% of tuberculosis growth at a concentration of 50 µM and inhibited 100% of TB growth at 100 µM. For comparison, minimal inhibitory concentrations (MICs) of currently utilized anti-TB drugs are given below.

| DRUG | MIC (µM) |
|---|---|
| Cycloserine | 147–195 |
| Pyrazinamide | 122 |
| Ethambutol | 5–25 |
| Streptomycin | 1.8–17 |
| Isoniazid | 1.5 |
| Viomycin | 1.5–15 |
| Ethionamide | 15 |

It is evident from the data shown above the HHC inhibition of TB growth falls within the range of MICs determined for clinically utilized anti-TB drugs and may actually fair better than some of these drugs.

The effect of HHC on various strains of drug resistant tuberculosis was determined using similar methods. The results indicate that HHC is able to inhibit 92% of Isoniazid and Rifampin Resistant TB at a concentration of 75 µM HHC; 98% of Pyrazinamide Resistant TB growth at 75 µM HHC; and 91% of Isoniazid Resistant TB growth at 75 µM HHC. Thus, HHC is effective in inhibiting the growth of a variety of drug resistant strains of tuberculosis.

Example VII—Determination of the Maximal Tolerated Dose (MTD) of HHC

Eight groups of BDF1 mice (5 animals/group) were used to determine a maximal tolerated dose (MTD) for HHC.
Group 1: no treatment
Group 2: DMSO (dimethylsulfoxide) treatment
Group 3: 50 µM HHC (1.7 mg HHC/kg)
Group 4: 100 µM HHC (3.3 mg HHC/kg)
Group 5: 150 µM HHC (4.9 mg HHC/kg)
Group 6: 200 µM HHC (6.5 mg HHC/kg)
Group 7: 400 µM HHC (13 mg HHC/kg)
Group 8: 800 µM HHC (26 mg HHC/kg)

All mice were weighed, the weight being used to determine blood volume for each animal. The amount of drug necessary to achieve a theoretical concentration of drug in the animal (e.g, 50, 100, 150 µM etc.) was calculated based on the formula: blood volume=8% body weight of the animal. Drug solutions were made using DMSO as the solvent and a single intraperitoneal injection of a volume of 100–120 µl was given. Animals were observed for survival/death. Based on the above, the MTD is determined to be at 200 µM (~6.5 mg/kg). To confirm the MTD, it is necessary to dose the animals with the predetermined MTD once a day for consecutive days following established experimental treatment times (i.e., 5 days for in vivo tumor inhibition studies).

Example VIII—Anti-Protozoal Activity (*Leishmania*)

*Leishmania tarentolae* was grown in BHI (brain heart infusion; Difco) supplemented with 10 µg/ml of hemin. Leishmanial cells were counted by doing a 1:1 dilution of the cells with 3% formaldehyde/1×SSC (0.15 M NaCl/0.015 M sodium citrate) solution. Cells were seeded at log phase (0.5–1×10$^6$ cells/ml) in T-25 cm$^2$ flasks. Equal volumes of HHC at different concentrations (0.1, 0.25, 0.5, 1.0, 2.5 µM) were added to the cells. DMSO at the same volume as that used for HHC was included as solvent control. At each time point (6, 12, 18, 24, 32 hrs post-drug addition), cells were observed under the microscope for possible effect of HHC on *Leishmanial* motility. Aliquots of cells (100 µl) were removed from each flask at each time point, diluted as mentioned above and cell numbers were quantitated using a hemocytometer. Results are shown in Table VI.

TABLE VI

| | cells/ml* 0 hr | cells/ml 6 hr | % control | cells/ml 12 hr | % control | cells/ml 18 hr | % control | cells/ml 24 hr | % control | cells/ml 32 hr | % control |
|---|---|---|---|---|---|---|---|---|---|---|---|
| control | 1.2 | 3.47 | 100 | 7.12 | 100 | 12.5 | 100 | 17.9 | 100 | 38.6 | 100 |
| 0.1 µM HHC | 1.2 | 2.65 | 76.4 | 6.58 | 96.6 | 12.1 | 96.8 | 21.2 | 118 | 43.9 | 114 |
| 0.25 µM HHC | 1.2 | 3.0* | 86.5 | 7.35 | 103 | 12.7 | 101 | 19.72 | 110 | 40.1 | 104 |
| 0.5 µM HHC | 1.2 | 2.43 | 70.0 | 5.13 | 72.1 | 9.22 | 73.8 | 14.2 | 79.3 | 29.2 | 75.6 |
| 1.0 µM HHC | 1.2 | 2.09 | 60.2 | 2.53 | 35.5 | 2.55 | 20.4 | 2.9 | 16.2 | 3.4 | 8.8 |
| 2.5 µM HHC | 1.2 | 1.81 | 52.2 | 3.03 | 42.6 | 3.38 | 27.0 | 2.13 | 11.9 | 2.82 | 7.3 |
| DMSO control | 1.2 | 3.01 | 86.7 | 7.07 | 99.3 | 13.9 | 111 | 22.2 | 124 | 42.8 | 111 |

*no. of cells × 10$^6$

What is claimed is:

1. A method comprising inhibiting the growth of *Staphylococcus aureus* or *Mycobacterium tuberculosis* bacteria by contacting the bacteria with an effective amount of a compound of formula (I):

wherein R is —CH(CH₃)₂; or a pharmaceutically acceptable salt thereof; wherein the bacteria is resistant to methicillin, ciproflaxacin, vancomycin, chloramphenicol, penicillin, aminoglycosides, erythromycin, cephalothin, cloxacillin, tetracycline, chloramphenicol, isoniazid, rifampin, pyrazinamide or ethambutol.

2. The method of claim 1 wherein the bacteria is resistant to methicillin, ciproflaxacin, vancomycin, chloramphenicol, penicillin or aminoglycoside.

3. The method of claim 1 wherein the bacteria is resistant to erythromycin, cephalothin, cloxacillin, tetracycline or chloramphenicol.

4. The method of claim 1 wherein the bacteria is resistant to isoniazid, rifampin, pyrazinamide or ethambutol.

5. The method of claim 2 wherein the bacteria is *Staphylococcus aureus*.

6. The method of claim 3 wherein the bacteria is *Staphylococcus aureus*.

7. The method of claim 4 wherein the bacteria is *Mycobacterium tuberculosis*.

8. A therapeutic method comprising inhibiting bacterial cell growth in a mammal infected with *Staphylococcus aureus* or *Mycobacterium Tuberculosis* bacteria by administering an effective amount of a compound of formula (I):

wherein R is —CH(CH₃)₂; or a pharmaceutically acceptable salt thereof; wherein the bacteria is resistant to methicillin, ciproflaxacin, vancomycin, chloramphenicol, penicillin, aminoglycosides, erythromycin, cephalothin, cloxacillin, tetracycline, chloramphenicol, isoniazid, rifampin, pyrazinamide or ethambutol.

9. The method of claim 8 wherein the bacteria is resistant to methicillin, ciproflaxacin, vancomycin, chloramphenicol, penicillin or aminoglycoside.

10. The method of claim 8 wherein the bacteria is resistant to erythromycin, cephalothin, cloxacillin, tetracycline or chloramphenicol.

11. The method of claim 8 wherein the bacteria is resistant to isoniazid, rifampin, pyrazinamide or ethambutol.

12. The method of claim 8 wherein the compound is administered to the mammal parenterally.

13. The method of claim 8 wherein the compound is administered to the mammal topically.

14. The method of claim 8 wherein the compound is administered to the mammal orally.

15. The method of claim 8 wherein the mammal is a human.

16. The method of claim 9 wherein the bacteria is *Staphylococcus aureus*.

17. The method of claim 10 wherein the bacteria is *Staphylococcus aureus*.

18. The method of claim 11 wherein the bacteria is *Mycobacterium tuberculosis*.

* * * * *

UNITED STATES PATENT AND TRADEMARK OFFICE
CERTIFICATE OF CORRECTION

PATENT NO. : 5,827,895
DATED : Oct. 27, 1998
INVENTOR(S) : Louise Nutter, et al.

It is certified that error appears in the above-identified patent and that said Letters Patent is hereby corrected as shown below:

Col. 15, line 17, delete "chloramphenicol".

Col. 15, line 35, replace "Tuberculosis" with --tuberculosis--.

Col. 16, line 5, delete "chloramphenicol".

Col. 5, line 38, replace "their its" with -- their--.

Col. 6, line 15, replace "multi-does" with --multi-dose--.

Col. 6, line 39, replace "4383,529 with "--4,383,529--.

Col. 6, line 43, replace "acadia" with --acacia--.

Signed and Sealed this

Twelfth Day of October, 1999

*Attest:*

Q. TODD DICKINSON

*Attesting Officer*  *Acting Commissioner of Patents and Trademarks*